United States Patent [19]
Guri et al.

[11] Patent Number: 5,750,402
[45] Date of Patent: May 12, 1998

[54] COMPOSITIONS AND METHODS TO PREVENT MICROBIAL CONTAMINATION OF PLANT TISSUE CULTURE MEDIA

[75] Inventors: Assaf Z. Guri, Cherry Hill, N.J.; Kishor N. Patel, Dobbs Ferry, N.Y.

[73] Assignee: Plant Cell Technology, Inc., Washington, D.C.

[21] Appl. No.: 460,703

[22] Filed: Jun. 2, 1995

[51] Int. Cl.$^6$ .............................. C12N 5/00; C12N 5/02
[52] U.S. Cl. .................. 435/431; 435/410; 435/420; 504/118
[58] Field of Search .................. 435/240.4, 431, 435/420, 410; 504/118

[56] References Cited

U.S. PATENT DOCUMENTS

| | | |
|---|---|---|
| 3,122,432 | 2/1964 | Biggs . |
| 3,523,121 | 8/1970 | Lewis et al. . |
| 3,761,488 | 9/1973 | Lewis et al. . |
| 4,105,431 | 8/1978 | Lewis et al. . |
| 4,243,403 | 1/1981 | Lewis et al. . |
| 4,252,694 | 2/1981 | Lewis et al. . |
| 4,265,899 | 5/1981 | Lewis et al. . |
| 4,279,762 | 7/1981 | Lewis et al. . |
| 4,454,146 | 6/1984 | Borovian . |
| 4,499,071 | 2/1985 | Borovian . |
| 4,540,570 | 9/1985 | Borovian . |
| 4,555,400 | 11/1985 | Borovian . |
| 5,028,620 | 7/1991 | Hsu . |
| 5,100,905 | 3/1992 | Hsu . |

FOREIGN PATENT DOCUMENTS

| | | |
|---|---|---|
| 4-63589 | 2/1992 | Japan . |
| 4-311326 | 11/1992 | Japan . |

OTHER PUBLICATIONS

Chapman, 1994, "An effective biocide for in vitro diagnostic reagents and other products", Am Clin Lab Aug. 1994, pp. 13–14.
Francko, 1986, "Studies on *Nelumbo lutea* (Willd.) Pers. I. Techniques for axenic liquid seed culture", Aquatic Botany 26:113–117.
Gilbert et al., 1991, "The use of antibiotics to eliminate latent bacterial contamination in potato tissue cultures", Ann Appl Biol 119:113–120.
Green, 1993, "Efficacy of biocides on laboratory-generated *Legionella* biofilms", Lett Appl Microbiol 17:158–161.
Gruvberger et al., 1986, "Demonstration of Kathon® CG in some commercial products", Contact Dermatitis 15:24–27.
Haack and Warwick, 1993, "Controlling microbial growth in aqueous-based pesticide formulations", in *Pesticide Formulations and Application Systems*, Devisetty et al. (eds.), pp. 105–115.
Haldeman et al., 1987, "Use of benomyl and rifampicin for in vitro shoot tip culture of *Camellia sinensis* and *C. japonica*", Hortscience 22(2):306–307.
Hall, 1988, "Comparative activity of selected food preservatives as citrus postharvest fungicides", Proc Fla State Hort Soc 101:184–187.
Idise and Izuagbe, 1985, "Effect of preservatives and pasteurization on microorganisms isolated from Nigerian bottled palm wine", Microbios Letters 28:117–121.
Kneifel and Leonhardt, 1992, "Testing of different antibiotics against Gram-positive and Gram-negative bacteria from plant tissue culture", Plant Cell, Tissue and Organ Culture 29:139–144.
Macek et al., 1994, "Chemical sterilization of nutrient media for plant cell cultures using diethylpyrocarbonate", Biotechnology Techniques 8(12):885–888.
The Merck Index, 10th Edition, 1983, Entry No. 7555 and No. 8413.
Phillips et al., 1981, "Antibiotics in plant tissue culture: Rifampicin effectively controls bacterial contaminants without affecting the growth of short-term explant cultures of *Helianthus tuberosus*", Plant Science Letters 21:235–240.
Pollock et al., 1983, "The toxicity of antibiotics to plant cell cultures", Plant Cell Reports 2:36–39.
Ryu and Holt, 1993, "Growth inhibition of *Penicillium expansum* by several commonly used food ingredients" J Food Protection 56(10)862–867.
Sodeko et al., 1987, "Effect of different preservative treatments on the microbial population of Nigerian orange juice", Microbios 51:133–143.

*Primary Examiner*—Leon B. Lankford, Jr.
*Attorney, Agent, or Firm*—Pennie & Edmonds LLP

[57] ABSTRACT

The present invention encompasses compositions and methods to reduce or prevent microbial growth in plant tissue culture media, comprising adding a chemical agent comprising methylchloroisothiazolinone, methylisothiazolinone, magnesium chloride and magnesium nitrate to a plant culture medium at a concentration that reduces or prevents microbial contamination of the plant tissue culture medium and that allows substantially normal germination of seeds or substantially normal growth or development of plants, plant organs, plant tissues or plant cells. The chemical agent may further comprise potassium sorbate or sodium benzoate, or both. The present invention further provides a kit for germinating plant seeds or culturing plants, plant organs, plant tissues or plant cells on a plant tissue culture medium comprising the chemical agent.

19 Claims, No Drawings

COMPOSITIONS AND METHODS TO PREVENT MICROBIAL CONTAMINATION OF PLANT TISSUE CULTURE MEDIA

1. FIELD OF THE INVENTION

The present invention relates to compositions and methods for the prevention or inhibition of microbial growth in culture media for plant tissue cultures which normally require maintenance of sterile conditions. Specific chemical agents are used in the culture medium at concentrations that reduce or prevent microbial contamination but which allow for substantially normal germination of seeds or substantially normal growth or development of plants, plant organs, plant tissues or plant cells. The disclosed compositions and methods are useful to researchers in plant tissue culture and plant molecular biology, as well as to plant breeders and plant nursery workers, and in a variety of commercial applications.

2. BACKGROUND OF THE INVENTION

2.1. IN VITRO PLANT CULTURE SYSTEMS

Plant growth and development are fundamental biological processes of great scientific, educational and commercial interest. These biological processes can be observed and manipulated by the germination of seeds and the propagation of whole plants, plant organs, plant tissues and plant cells in vitro in sterile culture on various types of culture media.

The practice of growing plants in vitro is well-developed. See, for example, Thorpe, T. A. (ed.), *Plant Tissue Culture: Methods and Applications in Agriculture*, Academic Press, Inc., New York (1981); Evans et al. (ed.), *Handbook of Plant Cell Culture*, Vol. 1, MacMillan Publishing Co., New York, London, (1983); and Dixon, R. A. (ed), *Plant Cell Culture: A Practical Approach*, IRL Press, Oxford, Washington DC (1985).

For normal growth and development, plants grown in vitro require, at a minimum, a medium containing essential mineral salts. See, for example, Salisbury, F. B. and Ross, C. W. *Plant Physiology*, 3d Ed., Wadsworth Publishing Co. (1985). In addition, cultured plant tissues and cells typically require various combinations of plant hormones (phytohormones), vitamins and one or more simple sugars. See Thorpe, supra.

Unfortunately, such culture media also provide a rich mixture of nutrients which can support the rapid growth of bacteria and fungi. Once these contaminants are established in culture they usually grow quickly, depleting the medium of nutrients and producing toxins that can affect the growth of, and ultimately kill, the cultured plant tissue.

Accordingly, the use of sterile techniques has been a strict requirement for all in vitro plant culture manipulations. For example, the preparation and maintenance of a standard tissue culture system requires the sterilization of the culture medium, either by heat or by filtration, the sterilization of the culture container, surface-sterilization of the seed or plant tissue to be cultured, and sterilization of any instruments used to handle or manipulate the plant tissue. In addition, any subsequent manipulation of the plant tissue must typically be carried out in a filtered-air environment, e.g., in a laminar-flow hood.

Despite the most stringent use of sterile techniques by the skilled artisan, however, the contamination of plant cultures remains a persistent problem that can result in losses ranging from small numbers of cultures to the catastrophic loss of whole batches of culture medium and tissue cultures. Contamination by bacteria and fungi is an insidious process that continually threatens plant tissue cultures throughout the duration of the culture period. Despite the fact that plant tissue cultures may be sterile when initiated, microorganisms can often contaminate cultures at any point during subsequent tissue culture manipulations. Thus, it would be useful to provide a chemical agent that reduces or prevents the microbial contamination of plant tissue culture media and maintains the sterility of the media for the duration of the culture period.

2.2. ANTIMICROBIAL AGENTS IN PLANT TISSUE CULTURE

Various types of antimicrobial chemical agents have been tested in plant tissue cultures. Antibiotics have been extensively tested for their ability to inhibit or prevent the growth of bacteria in plant cultures. However, the use of antibiotics has certain limitations. For example, antibiotics are expensive, they are only effective against bacteria and not fungi, their range of efficacy against types of bacteria is often narrow, they are usually heat-labile, and they are often phytotoxic or otherwise capable of altering the behavior of cultured plant tissues.

For example, Phillips, R., et al., *Plant Sci. Lett.*, 21: 235–240 (1981), describe tests of six antibiotics, i.e., benzyl penicillin, phosphomycin, chloramphenicol, streptomycin, rifampicin and nalidixic acid, on preventing bacterial infection in cultures of Jerusalem artichoke (*Helianthus tuberosus*). Only rifampicin was able to control bacterial contamination without affecting rates of plant cell division, cell differentiation or DNA synthesis in cultured explants. However, rifampicin triggered an increase in protein synthesis.

Pollock, K., et al., *Plant Cell Reports*, 2: 36–39 (1983), describe the toxicity of over twenty different antibiotics on the plating efficiency of protoplast-derived cells of *Nicotiana plumbaginifolia*. While the betalactams, i.e., the penicillins and the cephalosporins, had little observable toxic effect on the plating efficiency of the cells, these antibiotics stimulated plant cell colony growth. The aminoglycosides, e.g., streptomycin and kanamycin, by contrast, were clearly toxic to the plant cells. Erythromycin was relatively non-toxic to the plant cells, while the tetracyclines were very inhibitory in long-term toxicity tests.

Gilbert, J. E., et al., *Ann. Appl. Biol.*, 119: 113–120 (1991), describe the use of antibiotics to control latent bacterial contamination in potato cell cultures. Two different combinations of antibiotics, either penicillin, streptomycin and amphotericin or erythromycin, streptomycin and carbenicillin, were tested. Each combination, when added to media used to culture microplantlets, reduced plant growth and induced chlorosis at higher concentrations. Not only were the mixtures phytotoxic, but they failed to eliminate contamination. However, when the former mixture of antibiotics was added to enzyme media used to prepare protoplasts, contamination was apparently eliminated.

In addition to antibiotics, chemical biocides have been tested for their ability to inhibit or prevent microbial contamination in plant cultures.

For example, Macek, T., et al., *Biotechnology Techniques*, 8(12): 885–888 (1994), describe the use of diethylpyrocarbonate (DPC) to chemically sterilize nutrient media for plant cell cultures. DPC killed all contaminating microorganisms without changing the growth characteristics of cultured plant cells. However, since DPC decomposes to ethanol and carbon dioxide over a period of several hours when brought into contact with water, DPC cannot serve to maintain the sterility of plant cell cultures over the duration of the culture period.

Japanese Patent No. 4-311326 discloses a method of eliminating fungal contamination in tissue cultures of Cyclamen plants comprising dipping a tissue slice from a Cyclamen plant into a solution containing imidazole or triazole fungicide or culturing a tissue slice on culture medium containing the fungicide. However, this treatment does not serve to inhibit bacterial contamination.

Japanese Patent No. 4-63589 discloses the use of allyl isothiocyanate ($CH_2=CHCH_2N=C=S$) as a sterilizing agent in plant culture media, in which the chemical agent eliminated the need for autoclaving and no abnormality was observed in tissue cultures of Carnation plants.

Combinations of antibiotics and chemical biocides have been tested for their ability to inhibit microbial contamination in plant cultures.

For example, Francko, D. A., *Aquatic Botany*, 26: 113-117 (1986), describes the use of antibiotics (penicillin G and streptomycin sulfate) in combination with a fungicide (Captan) in an attempt to obtain axenic plants from seeds of the aquatic plant *Nelumbo lutea* (Willd.). Tests indicated that when these agents were included in the incubation media, roughly one-half of the seed cultures lacked detectable contaminants after two weeks of growth. However, only 11% of the initial cultures remained contaminant-free four weeks after transfer to fresh media lacking the antibiotics and fungicide.

Haldeman, J. H., et al., *Hortscience*, 22(2): 306-307 (1987), describe the use of a combination of a fungicide (benomyl) and an antibiotic (rifampicin) as a treatment to control persistent fungal and bacterial contamination in cultures of Camellia shoot tip explants from field-grown plants. A 24-hr treatment of shoot tips with this mixture after standard deinfestation treatments in bleach solution significantly reduced, but did not eliminate, contamination.

Kneifel, W. and Leonhardt, W., *Plant Cell, Tissue and Organ Culture*, 29: 139-144 (1992), describe tests of different combinations of antibiotics and chemical biocides against gram-positive and gram-negative bacteria isolated from plant tissue cultures. A mixture of Imipenem™ (N-Formimidoyl-thienanycin monohydrate; Merck, USA) and ampicillin, and a mixture of Imipenem™ and penicillin G, were found to be most effective at inhibiting bacterial contamination and had no obvious effect on growth rate or root growth, nor was any damage to chlorophyll evident. A mixture of IMIPENEM™ and KATHON™ (5-chloro-2-methyl-4-isothiazolin-3-one and 2-methyl-4-isothiazolin-3-one; Rohm & Haas, Austria), however, led to reduced root growth of two plant species tested.

A variety of other chemicals are recognized in the art as having general preservative or biocidal activity. Four of these chemicals which are useful in the present invention are potassium sorbate, sodium benzoate, methylchloroisothiazolinone and methylisothiazolinone.

The Merck Index (10th Ed., 1983, Entry No. 7555) lists potassium sorbate as a mold and yeast inhibitor, and sodium benzoate (Entry No. 8413) as a preservative, especially for food products. Ryu, D. and Holt, D. L., *J. Food Protection*, 56(10): 862-867 (1993), demonstrate that potassium sorbate inhibits the growth of *Penicillium expansum* in fungal culture and on apples. Hall, D. J., *Proc. Fla. State Hort. Soc.*, 101: 184-187 (1988), demonstrates that potassium sorbate and sodium benzoate are each effective as post-harvest fungicides on citrus. Idise, O. E. and Izuagbe, *Microbios Lett.*, 28: 117-121 (1985), demonstrate that sodium benzoate effectively inhibits the growth of bacteria and yeast in bottled palm wine. Sodeko, O. O., et al., *Microbios*, 51: 133-143 (1987), demonstrate that sodium benzoate effectively inhibits bacteria and fungi in orange juice. U.S. Pat. No. 3,122,432 to Biggs discloses a composition for preserving cut flowers which comprises several ingredients, including sodium benzoate which is described as a fermentation and mold inhibitor.

Methylchloroisothiazolinone and methylisothiazolinone, along with magnesium salts as stabilizers, comprise the biocide KATHON™ CG (Rohm & Haas, USA), which is widely used in a broad range of cosmetics, paints, air conditioning units, etc. Gruvberger, B., et al., *Contact Dermatitis*, 15: 24-27 (1986), describe chromatographic methods to detect KATHON™ CG in cosmetics. Haack, T. K. and Warwick, E. F., in: *Pesticide Formulations and Application Systems*, Devisetty, D. G., et al. (eds), Am. Soc. Testing and Materials, Philadelphia (1993), pp. 105-115, provide data regarding the agricultural preservative, Legend MK™, which is a different commercial embodiment of methylchloroisothiazolinone and methylisothiazolinone, and which is described therein as an effective antimicrobial agent for aqueous flowable pesticide formulations. Green, P. N., *Lett. Appl. Microbiol.*, 17: 158-161 (1993), demonstrates that of five commercial biocides tested, the mixture of methylchloroisothiazolinone and methylisothiazolinone was highly effective against laboratory-generated microbial biofilms of *Legionella bozemanii*. Chapman, J. S., *Am. Clin. Lab.*, pp. 13-14, (Aug. 1994), describes how a third commercial embodiment of a mixture of methylchloroisothiazolinone and methylisothiazolinone, marketed as ProClin™ (Rohm & Haas, distributed by Supelco, Inc.), is highly effective against a broad spectrum of least 14 different species of gram-negative bacteria, 9 different species of gram-positive bacteria, and 18 different species of fungi.

In addition, U.S. Pat. Nos. 3,523,121; 3,761,488; 4,105,431; 4,243,403; 4,252,694; 4,265,899; and 4,279,762 to Lewis disclose novel isothiazolones that are biocidally active against a broad range of microorganisms including bacteria, algae and fungi in a wide range of applications, including soaps, detergents, coatings, cosmetics, cutting oils, and as fungicides on seeds to be planted in soil.

Furthermore, U.S. Pat. Nos. 4,454,146; 4,499,071; 4,540,570; and 4,555,400 to Borovian disclose synergistic preservative compositions for inhibiting the growth of microorganisms, which compositions comprise at least two components, the first of which is selected from a group of one or more traditional preservatives, including benzoic acid, sorbic acid, and a mixture of methylchloroisothiazolinone and methylisothiazolinone, and a second component which is a polycyclic compound defined therein which, in combination with the first component, kills or inhibits microorganisms synergistically.

Finally, U.S. Pat. Nos. 5,028,620 and 5,100,905 to Hsu disclose a synergistic biocide composition with decreased sensitization potential, the first component of which is methylchloroisothiazolinone in the range of about 1.2 to 25.4%, and the second component of which is methylisothiazolinone in the range of about 74.6 to about 98.8%.

Although these four components, i.e., potassium sorbate, sodium benzoate, methylchloroisothiazolinone and methylisothiazolinone, are known to have preservative or biocidal activities, there is no teaching or suggestion in the art that these chemicals, or any combination thereof, would be useful to reduce or prevent microbial contamination in plant tissue cultures without negatively affecting the plant tissues. In fact, the report by Kneifel, W. and Leonhardt, W., supra, of reduced root growth on a mixture of IMIPENEM™ and KATHON™ teaches away from the use of KATHON™-containing agents in plant tissue cultures.

It would be beneficial to provide additional chemical agents that could be added to plant tissue culture media, which agents would reduce or prevent bacterial and fungal contamination for the duration of the culture period, and which would allow for substantially normal germination of seeds or substantially normal growth or development of cultured seeds, plants, plant organs, plant tissues or plant cells.

3. SUMMARY OF THE INVENTION

It is an objective of the present invention to provide compositions and methods for reducing or preventing microbial contamination of in vitro plant tissue cultures throughout the culture period. Such objective can be achieved by incorporating a chemical agent into a plant culture medium at a concentration that effectively reduces or prevents the growth of bacteria and fungi and that allows for substantially normal germination of seeds or substantially normal growth or development of plants, plant organs, plant tissues or plant cells.

It is a further objective of the present invention to provide a plant tissue culture medium comprising a chemical agent in a concentration that is effective to reduce or prevent microbial contamination throughout the culture period and that allows for substantially normal germination of seeds or substantially normal growth or development of plants, plant organs, plant tissues or plant cells.

It is a further objective of the present invention to provide a kit for culturing seeds, plants, plant organs, plant tissues or plant cells on a plant tissue culture medium comprising a chemical agent in a concentration that is effective to reduce or prevent microbial contamination throughout the culture period and that allows for substantially normal germination of seeds or substantially normal growth or development of plants, plant organs, plant tissues or plant cells, which kit comprises a culture container comprising a plant tissue culture medium comprising the chemical agent, in which the culture medium is either already prepared, i.e., ready for immediate use, or is ready to be prepared, for example, by the addition of water. The kit further comprises one or more plant seeds which have preferably been surface-sterilized, or one or more plants, plant organs, plant tissues or plant cells.

4. DETAILED DESCRIPTION OF THE INVENTION

The present invention provides compositions and methods for reducing or preventing microbial contamination of in vitro plant cultures throughout the culture period. A chemical agent is incorporated into a plant culture medium in a concentration that is effective to reduce or prevent the growth of bacteria and fungi and that allows for substantially normal germination of seeds or substantially normal growth or development of plants, plant organs, plant tissues or plant cells.

The chemical agent useful in practicing the present invention preferably comprises a mixture of methylchloroisothiazolinone (5-chloro-2-methyl-4-isothiazolin-3-one), methylisothiazolinone (2-methyl-4-isothiazolin-3-one), magnesium chloride and magnesium nitrate. More preferably, the chemical agent comprises a mixture of methylchloroisothiazolinone, methylisothiazolinone, magnesium chloride, magnesium nitrate, and potassium sorbate or sodium benzoate. Most preferably, the chemical agent comprises a mixture of methylchloroisothiazolinone, methylisothiazolinone, magnesium chloride, magnesium nitrate, potassium sorbate and sodium benzoate.

Applicants have surprisingly discovered that these combinations of chemicals, in a particular range of concentrations, are effective in reducing or preventing microbial contamination in plant tissue cultures for the duration of the tissue culture period, but allow for substantially normal germination of seeds or substantially normal growth or development of plants, plant organs, plant tissues or plant cells.

The relative concentrations of the individual components comprising the chemical agent may be varied to produce a mixture that is optimally effective in practicing the method of the present invention for any particular plant culture medium, plant species, plant seed, plant, plant organ, plant tissue or plant cell. However, a preferred mixture of the components in the chemical agent comprises: methylchloroisothiazolinone in a concentration range of about 2.0 to about 2.6 g/l; methylisothiazolinone in a concentration range of about 0.6 to about 0.8 g/l; magnesium chloride in a concentration range of about 15.0 to about 30 g/l; and magnesium nitrate in a concentration range of about 15.0 to about 30 g/l.

A more preferred mixture of the components in the chemical agent further comprises: potassium sorbate in a concentration range of about 15 to about 25 g/l or sodium benzoate in a concentration range of about 13 to about 27 g/l.

A most preferred mixture of the components in the chemical agent further comprises: potassium sorbate in a concentration range of about 15 to about 25 g/l; and sodium benzoate in a concentration range of about 13 to about 27 g/l.

In all cases, the components of the chemical agent are mixed to form a stock solution of chemical agent using any liquid in which the components will dissolve, but preferably in water, and most preferably in distilled or deionized water.

As used in the present application, "plant tissue culture" or "culturing plant tissues" refers to any process carried out in vitro wherein seeds are germinated, or plants, plant organs, plant tissues or plant cells are propagated, differentiated, subcultured or otherwise maintained on a culture medium, defined or undefined, which typically is maintained in a sterile (syn: aseptic, axenic) condition, i.e., free of microbial contamination, and generally is incubated under controlled environmental conditions.

As used in the present application, "microbial contamination" refers to the growth of any unwanted microorganisms, e.g., bacteria or fungi, in a plant tissue culture.

As used in the present application, the terms "plant tissue culture medium," "plant culture medium," "culture medium," and "medium" refer to a solid substrate or liquid solution in which a plant seed will germinate, a plant can be maintained or grown, an isolated plant organ or plant tissue can be maintained, propagated or differentiated, or one or more isolated plant cells, plant cell aggregates or plant cell protoplasts may be maintained, propagated, or differentiated, and which is to be maintained in a sterile condition, i.e., substantially free of microbial contamination.

The terms "plant tissue culture medium," "plant culture medium," "culture medium," and "medium" are further intended to refer to water containing an appropriate mixture of mineral salts. The culture medium may further incorporate, in appropriate concentrations, phytohormones including, for example, auxins, cytokinins or gibberellins, vitamins, such as one or more B-vitamins, one or more carbon sources including, for example, sucrose or glucose, and one or more undefined growth enhancers, such as coconut milk. The components of the mineral salts mixture may be selected and prepared in accordance with the requirements of the particular plant species being propagated. The appropriate composition of the mineral salts may either be empirically determined or selected from mineral salt compositions previously known in the plant tissue culture art and prepared accordingly. Alternatively, the mineral salts may be selected from any number of commercially available mixtures (e.g., from Sigma Chemical Co., St. Louis, Mo.). Mineral salt mixtures useful in the practice of the present invention include, for example, Hoagland's basal salt mixture, Gamborg's B-5 basal salt mixture, Heller's basal salt mixture, Murashige and Skoog basal salt mixture, Nitsch and Nitsch basal salt mixture, White's basal salt mixture, and variations thereof. In addition, various macronutrients, micronutrients and vitamin components known in the art may be variously combined to produce a culture medium appropriate to the plant species being propagated.

According to the method of the present invention, the chemical agent is added to the plant tissue culture medium in a concentration that will reduce or prevent the growth of bacteria or fungi, or both, and that will allow substantially normal seed germination or substantially normal growth or development of a plant, plant organ, plant tissue or plant cell cultured thereon.

As used in the present invention, a chemical agent is effective at reducing or preventing microbial growth in a plant culture medium if addition of the chemical agent to the plant culture medium at a concentration that allows substantially normal seed germination or growth or development of plants, plant parts, plant tissues or plant cells, reduces the amount of bacterial or fungal contamination by at least 80% compared to control media lacking the chemical agent.

According to the present invention, substantially normal germination of seeds is defined as a germination percentage that is at least 50% of the germination percentage on control culture medium not containing the chemical agent.

According to the present invention, substantially normal growth of a plant, plant organ, plant tissue or plant cell is defined as a growth rate or rate of cell division of the plant, plant organ, plant tissue, or plant cell that is at least 50% of the growth rate or rate of cell division in a corresponding plant, plant organ, plant tissue or plant cell on control culture medium not containing the chemical agent.

According to the present invention, substantially normal development of a plant, plant organ, plant tissue or plant cell is defined as the occurrence of one or more developmental events in the plant, plant organ, plant tissue or plant cell that are substantially the same as those occurring in a corresponding plant, plant organ, plant tissue or plant cell on control culture medium not containing the chemical agent.

Generally, the chemical agent useful in the method of the present invention will be effective in a range of concentrations in the culture medium that allow for substantially normal seed germination or substantially normal growth or development of a plant, plant organ, plant tissue or plant cell cultured thereon. A preferred range of concentrations of the chemical agent in the culture medium is from about 0.01% to about 0.20% (v/v). A more preferred range of concentrations of the chemical agent in the culture medium is from about 0.02% to about 0.10% (v/v). The most preferred range of concentrations of the chemical agent in the culture medium is from about 0.03% to about 0.05% (v/v).

For those plant seeds, plants, plant organs, plant tissues or plant cells from any species for which the above ranges are not satisfactory, the optimal effective concentration of the chemical agent in the culture medium for use in the claimed method may be determined empirically by growing said seed, plant, plant organ, plant tissue or plant cell in a plant tissue culture medium at a range of concentrations of the chemical agent, and selecting one or more concentrations at which microbial contamination is reduced or prevented but that allows substantially normal seed germination, or that allows substantially normal growth or development of the plant, plant organ, plant tissue, or plant cell. Such an empirical determination may be carried out without undue experimentation using standard techniques for seed germination, or propagation of plants, plant organs, plant tissues or plant cells, in combination with routine screening techniques known to those skilled in the art.

For example, plant tissue culture media can be prepared according to any standard recipe for plant tissue culture media known in the art, with the chemical agent added in a range of concentrations for screening, as well as without chemical agent (control). Plant seeds may be "planted" in these media, appropriately incubated, and examined after a sufficient period of time to determine germination percentage. In addition, an evaluation of the growth or development of roots and shoots from germinated seeds as determined, for example, using any morphological, anatomical or biochemical characteristics, may be made by comparing seeds germinated on culture media comprising chemical agent to seeds germinated on control media lacking chemical agent.

The skilled artisan will be aware of and able to apply various morphological, anatomical, physiological and biochemical assays that are useful to determine the effects of chemical agents on the growth of plants. For example, a morphological analysis may comprise a comparison of the shape, size or number of roots, shoots, leaves or reproductive organs, or parts thereof. An anatomical analysis may comprise, for example, a comparative analysis of the size, shape, pattern or differentiation of cells, such as, for example, the amount, location or maturation of vascular tissues, trichomes, or stomata, or the presence or absence of actively dividing meristems. A physiological analysis may comprise, for example, a comparative analysis of the rates of respiration, photosynthesis, stomatal resistance or ethylene production. A biochemical analysis may comprise, for example, a comparative analysis of protein or DNA synthesis, chlorophyll degradation or the presence, absence, or amount of other pigments. One or more of these assays, all of which are known to the skilled artisan, can contribute to an empirical determination of the optimal concentration of the chemical agent in plant tissue culture medium to practice the method of the present invention on a particular plant species.

Once the optimal concentration of the chemical agent for practicing the method of the present invention is determined, it may be added to a culture medium that is thereafter to be used in liquid form for liquid cultures, including, for example, cell suspension cultures or protoplast cultures, or that is thereafter solidified by addition of a gelling agent. The culture medium is then typically adjusted to an appropriate pH, for example, pH 5.8, using appropriate acidic or basic solutions, e.g., hydrochloric acid (HCl) or potassium hydroxide (KOH).

In those instances where the culture medium is to be solidified, a gelling agent, for example, PHYTAGEL™ gellan gum (Sigma Chemical Co.), in an appropriate concentration range, for example, from 0.2% to 0.3% (w/v) for gellan gum, may be added to the culture medium. The culture medium must then be sufficiently heated, e.g., by autoclaving, to dissolve the gelling agent. The presence of the chemical agent, however, renders autoclaving for the purpose of sterilization unnecessary.

The antimicrobial activity of culture medium comprising the chemical agent is not reduced by autoclaving (121° C., 15 min). In addition, Applicants have discovered that plant culture medium comprising the chemical agent that has been autoclaved is less inhibitory to plant seed germination or to the growth or development of plants, plant organs, plant tissues or plant cells, as compared to the same culture medium comprising chemical agent that has not been autoclaved. However, this does not mean that autoclaving is strictly required to practice the invention, only that the range of concentrations of chemical agent in the culture medium useful to practice the present invention may be lower in some cases where the culture medium has not been autoclaved.

After autoclaving, culture medium comprising chemical agent and the dissolved gelling agent may then be transferred to individual culture containers of any type useful in the art and the medium allowed to cool and solidify.

An additional benefit of the chemical agent is that, where autoclaving is not needed to dissolve a gelling agent, heat-labile components of the culture medium such as vitamins and sugars will no longer require filter-sterilization. The culture medium so prepared may be stored for an extended period of time or used immediately.

Batches of culture media can be subdivided by transfer to one or more culture containers useful in the art, including flasks, beakers, square-sided containers, screw-cap jars, culture tubes or any other containers that are useful to culture seeds, plants, plant organs, plant tissues or plant cells. Culture containers may be composed of glass including, for example, borosilicate glass or soda glass, as well as plastics including, for example, transparent polystyrene or polypropylene. Culture containers should generally be clean, i.e., free of lint, dust or chemical residue; however, the addition of the chemical agent to the culture medium renders the sterilization of the culture containers by heat, radiation or other chemical means unnecessary.

Any plant seed, whole plant, isolated plant organ, plant tissue or plant cell can be cultured in plant tissue culture medium containing the chemical agent. For example, seeds of any plant species can be germinated in the culture medium of the invention. Such seeds can come from any species of dicotyledonous, monocotyledonous or gymnospermous plant, including any woody plant species that grows as a tree or shrub, any herbaceous species, or any species that produces edible fruits, seeds or vegetables, or any species that produces colorful or aromatic flowers. For example, the seed, whole plant, isolated plant organ, plant tissue or plant cell may be selected from a species of plant from the group consisting of cucumber, Morning Glory, balsam, pepper, eggplant, marigold, lotus, cabbage, daisy and Carnation. In addition, for purposes of this invention, the term "plant seed" encompasses the spores of ferns and other lower vascular plants, as well as the spores of non-vascular plants such as mosses, liverworts and hornworts.

Despite the anti-microbial nature of the chemical agent, it is preferred that prior to placing a seed, plant or plant organ in the culture medium to initiate a new culture, the seed, plant or plant organ should be surface-sterilized to remove the fungal or bacterial spores that are often initially present in relatively high density thereon. Techniques for surface-sterilization of seeds, plants and plant organs are well-known in the art, and can be accomplished using any generally available sterilizing agent, but household bleach (sodium hypochlorite solution) diluted in water is preferred. For example, one or more seeds may be effectively surface-sterilized by immersion in a dilute solution of household bleach in water at a concentration, for example, of about 5% to about 20% (v/v) bleach, with or without a surfactant, for a time sufficient to surface-sterilize the seeds, for example, from about 10 min to about 120 min. The seeds are then preferably rinsed 3 times with water.

Plant organs that may be cultured according to the method of the present invention include, but are not limited to, leaves, stems, roots, vegetative buds, floral buds, meristems, embryos, cotyledons, endosperm, sepals, petals, pistils, carpels, stamens, anthers, pollen, pollen tubes, ovules, ovaries and fruits, or sections, slices or discs taken therefrom.

Plant tissues that may be cultured according to the present invention include, but are not limited to, callus tissues, ground tissues, vascular tissues, storage tissues, meristematic tissues, leaf tissues, shoot tissues, root tissues, gall tissues, plant tumor tissues, and reproductive tissues.

Plant cells that may be cultured on the culture medium of the present invention include, but are not limited to, isolated cells with cell walls, variously sized aggregates thereof, and protoplasts.

Any plants, plant organs, plant tissues or plant cells that have been cultured in vitro on the culture medium of the invention can be transferred, i.e., subcultured, to fresh culture medium comprising the chemical agent at appropriate times for continued growth, development or differentiation in vitro. The present invention provides an additional benefit in that the subculturing of plant tissues or plant cells can be carried out without strict adherence to sterile techniques or use of a sterile work environment such as a laminar flow hood.

The present invention contemplates that cultured plants, plant organs, plant tissues, and plant cells can be transferred from the culture medium of the present invention to culture medium that does not comprise the chemical agent, or vice versa, as appropriate.

The present invention further contemplates that an intact plant or plant organ that has been cultured, regenerated, or otherwise maintained on the culture medium of the present invention can subsequently be removed from the in vitro tissue culture environment and transferred to a substrate, for example, soil or vermiculite, for continued growth and development outside of the in vitro environment.

The present invention further provides a kit for culturing seeds, plants, plant organs, plant tissues or plant cells on a plant tissue culture medium comprising a chemical agent in a concentration that is effective to reduce or prevent microbial contamination throughout the culture period and that allows for substantially normal germination of seeds or substantially normal growth or development of plants, plant organs, plant tissues or plant cells, which kit comprises a culture container comprising a plant tissue culture medium comprising the chemical agent, in which the culture medium is either already prepared, i.e., ready for immediate use, or is ready to be prepared, for example, by the addition of water. The kit further comprises one or more plant seeds which have preferably been surface-sterilized, or one or more plants, plant organs, plant tissues or plant cells.

Having now generally described the invention, the same will be more readily understood through reference to the following examples which are provided by way of illustration, and are not intended to be limiting of the present invention.

5. EXAMPLE: INHIBITORY EFFECT OF THE CHEMICAL AGENT ON MICROBIAL CONTAMINATION

The following experiments were carried out to test the antimicrobial effect of increasing concentrations of the chemical agent in a plant tissue culture medium.

A standard plant culture medium was prepared consisting of Murashige and Skoog mineral salts, 2% (w/v) sucrose, 0.4% (w/v) Gelrite™, adjusted to pH 5.8 with KOH, and either with or without the chemical agent as described below.

In a first set of experiments, chemical agent comprising the following components was prepared for incorporation into the culture medium prior to autoclaving:

| | |
|---|---|
| Methylchloroisothiazolinone | 2.3 g |
| Methylisothiazolinone | 0.7 g |
| Magnesium chloride | 23.0 g |
| Magnesium nitrate | 23.0 g |
| Potassium sorbate | 20.0 g |
| Sodium benzoate | 20.0 g |

Different concentrations of the above chemical agent in the culture medium were tested to determine the optimal concentrations for anti-microbial activity. For example, a range of concentrations of the chemical agent of 0.2 to 1.0% (v/v) in the culture medium was tested in 0.1% increments. A range of concentrations of the chemical agent of 0.1 to 0.2% (v/v) in the culture medium was tested in 0.025% increments. Finally, a range of concentrations of the chemical agent of 0.01 to 0.1% in the culture medium was tested in 0.01% increments.

After addition of the chemical agent, the culture medium was autoclaved (15 min, 121° C.) to dissolve the gelling agent. All subsequent manipulations were carried out under non-sterile conditions. Culture media containing the chemical agent were poured into non-sterile polystyrene containers, capped with non-sterile closures, and allowed to solidify. Culture medium that did not contain the chemical agent was poured into either non-sterile containers (control A) or into sterile containers (control B), with the containers capped with non-sterile and sterile closures, respectively, and allowed to solidify. Ten containers containing culture medium comprising the chemical agent at each concentration and 10 containers of control A medium were incubated for 7 days at 28° C. in the dark. After a week, no microbial contamination was evident in any container containing culture medium comprising the chemical agent. By contrast, microbial contamination was evident in all control A containers, which contained an average of 6.5 colonies of fungi and bacteria, total, per container.

In a second experiment, 10 containers containing culture medium comprising the chemical agent at each concentration, and 10 control B containers, were uncapped and left exposed to the outside air for 8 hrs. The containers were recapped and incubated for 7 days at 28° C. in the dark. No microbial contamination was evident in any container containing medium with the chemical agent, with the exception of two containers containing the lowest concentration of chemical agent, i.e., 0.01% (v/v), each of which contained a single fungal colony on the surface of the medium. By contrast, all control B containers were contaminated, containing an average of 2.5 colonies of fungi and bacteria, total, per container.

Additional experiments were carried out to test the effectiveness of different formulations of chemical agent. A first chemical agent was prepared comprising all six components used in the chemical agent formulated above, i.e., methylchloroisothiazolinone, methylisothiazolinone, magnesium chloride, magnesium nitrate, potassium sorbate and sodium benzoate, each in the same concentration as above. A second chemical agent was prepared comprising the same components in the same concentrations as above, but lacking sodium benzoate. A third chemical agent was prepared comprising the same components in the same concentrations as above, but lacking potassium sorbate. A fourth chemical agent was prepared comprising the same components in the same concentrations as above, but lacking both potassium sorbate and sodium benzoate. A fifth chemical agent was prepared comprising only potassium sorbate and sodium benzoate in the same concentrations as above. A sixth chemical agent was prepared comprising only potassium sorbate in the same concentration as above. A seventh chemical agent was prepared comprising only sodium benzoate in the same concentration as above.

Plant culture media were prepared as above. The seven different chemical agents prepared as above were incorporated into different batches of plant culture medium as above to a final concentration of 0.035% (v/v) in all media except controls. All plant culture media were then autoclaved (121° C., 15 min). The plant culture media comprising the different chemical agents were poured into 10 non-sterile polystyrene containers each and capped with non-sterile lids. Control culture medium without chemical agent was also prepared as above. The containers were incubated for 14 days at 27° C. in the dark.

After incubation, the 10 containers with control culture medium had a total of 82 microbial colonies (0% effective). Culture medium comprising the first chemical agent (all six components present) had no microbial colonies (100% effective). Culture medium comprising the second chemical agent, which lacked only sodium benzoate, had 7 microbial colonies (91% effective). Culture medium comprising the third chemical agent, which lacked only potassium sorbate, had 10 microbial colonies (88% effective). Culture medium comprising the fourth chemical agent, which lacked both potassium sorbate and sodium benzoate, had 13 microbial colonies (84% effective). Culture medium comprising the fifth chemical agent which comprised only potassium sorbate and sodium benzoate had 31 microbial colonies (62% effective). Culture medium comprising the sixth chemical agent which comprised only potassium sorbate had 55 microbial colonies (33% effective). Finally, culture medium comprising the seventh chemical agent which comprised only sodium benzoate had 65 microbial colonies (21% effective).

These results indicate that several formulations of chemical agent are effective at reducing or preventing the growth of bacteria and fungi in plant culture media under non-sterile conditions. However, to be effective according to the present invention the components methylchloroisothiazolinone, methylisothiazolinone, magnesium chloride and magnesium nitrate must be included in the chemical agent.

6. EXAMPLE: EFFECT OF THE CHEMICAL AGENT ON SEED GERMINATION

The following experiments were carried out to test the effects of increasing concentrations of chemical agent in a plant culture medium on seed germination and the subsequent growth of shoots and roots. Chemical agent used for these experiments comprised methylchloroisothiazolinone, methylisothiazolinone, magnesium chloride, magnesium nitrate, potassium sorbate and sodium benzoate, was formulated as described above for the first set of experiments in Section 5, and was incorporated into culture medium as above. The culture media were then autoclaved (121° C., 15 min).

Seeds from 10 species of plants were either surface-sterilized or not surface-sterilized. Seeds to be surface-sterilized were immersed in 20–40% (v/v) household bleach solution for 30 min and rinsed 3 times with regular non-sterile tap water. Seeds were then inserted approximately 1/10th inch into solidified culture medium comprising chemical agent at each concentration. One hundred seeds were tested for each plant species at each concentration of chemical agent. The containers were incubated for 7 days at 28° C. in the dark, and screened for both microbial contamination and seed germination percentage.

Regarding microbial contamination, at concentrations of the chemical agent of 0.4% (v/v) and less, colonies of bacteria and fungi appeared on approximately 86% of the seeds that were not surface-sterilized, while surface-sterilized seeds remained free of any microbial contamination at all concentrations.

The effect of chemical agent concentration on seed germination percentage varied with plant species. For example, at 1.0% (v/v) concentration of chemical agent, surface-sterilized cucumber seeds germinated at a high percentage (72%), while the germination of surface-sterilized lotus seeds was dramatically reduced (5%) (Table 1). The germination percentage of surface-sterilized seeds for all species remained high (>50%) at concentrations of chemical agent up to and including 0.2% (v/v).

These results indicate that the addition of chemical agent to the culture medium up to a concentration of 0.2% (v/v) allows for substantially normal seed germination in all species tested, but that some species, e.g., cucumber, Morning Glory, Balsam, etc., exhibit substantially normal germination up to a chemical agent concentration in the medium of 1.0% (v/v). In addition, these results indicate that surface-sterilization of seeds is preferred for the chemical agent in the culture medium to express its optimal effect on reducing or preventing microbial contamination of plant tissue cultures, due to the high density of bacterial and fungal spores normally present on the seeds of most plant species.

It is noteworthy that seeds that were not surface-sterilized generally had higher percentages of germination than seeds of the same species that were surface-sterilized (Table 1). This difference was more apparent in media containing concentrations of chemical agent of 0.2% (v/v) and higher, and may be the result of the bleach rendering the seed coat more permeable, thereby making the seed more sensitive to the chemical agent.

Regarding the subsequent growth of shoots and roots from germinating seeds, at concentrations of the chemical agent of 0.3% (v/v) and higher, for all species either no roots grew from the germinating seeds or the roots that grew were stunted in their growth and development (Table 2). Normal growth and development of both shoots and roots was observed in all plant species in culture media containing a concentration of chemical agent of 0.05% or less.

These results indicate that while a concentration of 0.05% (v/v) of chemical agent or less in the culture medium allows for substantially normal growth and development of shoots and roots in all species tested, some species, i.e., cucumber and cabbage, can produce substantially normal shoots and roots in culture medium containing chemical agent in a concentration up to 0.2% (v/v). As described above in Section 4, the optimal concentration of chemical agent for other plant species may be determined empirically and without undue experimentation.

7. EXAMPLE: EFFECT OF THE CHEMICAL AGENT ON ORGANOGENESIS FROM CALLUS TISSUE

The following experiments were carried out to test the effects of increasing concentrations of chemical agent in culture media on organogenesis from callus tissue. The chemical agent used for these experiments comprised methylchloroisothiazolinone, methylisothiazolinone, magnesium chloride, magnesium nitrate, potassium sorbate and sodium benzoate, as formulated above.

Leaves of eggplant (cv. Black Beauty) from plants grown in vitro were cut into small squares (approx. 1×1 cm) using sterile techniques. Ten leaf squares were incubated on culture medium containing Murashige and Skoog mineral salts, vitamins, including thiamine, pyridoxine and nicotinic acid, 3% sucrose (w/v), 2 mg/l naphthalene acetic acid (NAA) and 0.8% agar (w/v) (control medium) at pH 5.8, which medium had been autoclaved (121° C., 15 min) prior to use. Ten leaf squares each were incubated on the same type of culture medium as above, but further comprising either 0.03% or 0.04% (v/v) chemical agent. The cultures were incubated in the dark at 27° C. After 30–40 days, approximately 50 mg of white callus tissue had proliferated on all leaf squares on all media.

The callus tissue was separated from each of the leaf squares and subcultured on fresh culture media prepared as above, except that trans-zeatin (2 mg/l) replaced NAA. The callus tissues were subcultured at 27° C., with a light treatment of 10,000 ft-candles for 10 hrs per day. After 37 days, callus tissues on all media regenerated an average of 28 shoots per callus tissue. The shoots were separated from the callus tissues and inserted into fresh culture medium prepared as above, but lacking any phytohormones. All shoots regenerated roots on all culture media.

These results indicate that the addition of an antimicrobially effective concentration of chemical agent to the culture medium did not negatively affect callus induction, callus proliferation, or plant regeneration.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

All publications cited above are herein incorporated by reference.

TABLE 1

Percent Seed Germination On Increasing Concentrations Of Chemical Agent[†]

| Plant Type[*] | | 0 | 0.01 | 0.02 | 0.03 | 0.04 | 0.05 | 0.06 | 0.07 | 0.08 | 0.09 | 0.1 | 0.125 | 0.15 | 0.175 | 0.2 | 0.3 | 0.4 | 0.5 | 0.6 | 0.7 | 0.8 | 0.9 | 1.0 |
|---|---|---|---|---|---|---|---|---|---|---|---|---|---|---|---|---|---|---|---|---|---|---|---|---|
| Cucumber | S | 96 | 96 | 97 | 98 | 96 | 96 | 95 | 96 | 93 | 92 | 93 | 93 | 90 | 90 | 84 | 78 | 75 | 75 | 72 | 72 | 73 | 73 | 72 |
| | N | 98 | 98 | 99 | 99 | 97 | 96 | 96 | 96 | 98 | 98 | 97 | 96 | 97 | 94 | 90 | 90 | 91 | 90 | 90 | 88 | 89 | 88 | 89 |
| Morning Glory | S | 88 | 88 | 87 | 88 | 89 | 86 | 85 | 87 | 86 | 85 | 84 | 85 | 82 | 83 | 79 | 78 | 74 | 72 | 71 | 72 | 70 | 70 | 70 |
| | N | 92 | 93 | 91 | 92 | 90 | 91 | 93 | 92 | 91 | 93 | 92 | 90 | 91 | 90 | 89 | 89 | 89 | 87 | 86 | 85 | 85 | 86 | 86 |
| Balsam | S | 97 | 97 | 97 | 96 | 95 | 94 | 96 | 95 | 94 | 94 | 94 | 92 | 91 | 92 | 91 | 89 | 88 | 88 | 86 | 84 | 83 | 81 | 80 |
| | N | 99 | 99 | 99 | 100 | 98 | 98 | 97 | 96 | 95 | 96 | 96 | 97 | 93 | 94 | 92 | 91 | 90 | 91 | 89 | 89 | 87 | 88 | 87 |
| Pepper | S | 90 | 90 | 91 | 90 | 91 | 89 | 86 | 88 | 88 | 86 | 87 | 86 | 85 | 84 | 85 | 73 | 68 | 60 | 51 | 32 | 21 | 12 | 8 |
| | N | 92 | 93 | 92 | 92 | 91 | 91 | 91 | 92 | 90 | 91 | 92 | 90 | 91 | 90 | 88 | 82 | 80 | 80 | 79 | 77 | 76 | 75 | 72 |
| Egg Plant | S | 91 | 90 | 92 | 90 | 91 | 92 | 91 | 90 | 89 | 91 | 90 | 90 | 91 | 90 | 82 | 72 | 67 | 61 | 52 | 34 | 22 | 11 | 6 |
| | N | 92 | 93 | 92 | 94 | 92 | 91 | 91 | 90 | 90 | 92 | 91 | 90 | 89 | 88 | 87 | 80 | 80 | 78 | 77 | 72 | 74 | 72 | 70 |
| Marigold | S | 90 | 89 | 89 | 89 | 90 | 88 | 82 | 80 | 81 | 79 | 78 | 75 | 74 | 76 | 72 | 70 | 69 | 62 | 48 | 32 | 28 | 9 | 5 |
| | N | 98 | 97 | 93 | 94 | 95 | 92 | 93 | 91 | 90 | 90 | 90 | 87 | 82 | 83 | 80 | 77 | 76 | 75 | 72 | 68 | 66 | 52 | 46 |
| Lotus | S | 82 | 81 | 81 | 80 | 81 | 80 | 79 | 78 | 76 | 77 | 77 | 75 | 73 | 72 | 72 | 70 | 51 | 43 | 28 | 20 | 12 | 7 | 5 |
| | N | 85 | 85 | 84 | 85 | 83 | 84 | 82 | 84 | 82 | 81 | 83 | 80 | 81 | 82 | 80 | 77 | 71 | 70 | 65 | 60 | 52 | 48 | 32 |
| Cabbage | S | 81 | 82 | 81 | 81 | 78 | 78 | 79 | 78 | 78 | 77 | 76 | 75 | 74 | 73 | 71 | 71 | 72 | 70 | 70 | 69 | 65 | 63 | 61 |
| | N | 83 | 84 | 82 | 83 | 82 | 81 | 82 | 81 | 82 | 83 | 83 | 82 | 79 | 80 | 81 | 79 | 78 | 72 | 72 | 70 | 70 | 69 | 63 |
| Daisy | S | 76 | 74 | 74 | 74 | 72 | 73 | 70 | 71 | 68 | 69 | 61 | 60 | 59 | 57 | 58 | 46 | 40 | 31 | 27 | 21 | 17 | 12 | 6 |
| | N | 81 | 81 | 80 | 80 | 81 | 81 | 80 | 78 | 79 | 80 | 77 | 76 | 74 | 75 | 75 | 76 | 70 | 68 | 68 | 66 | 62 | 60 | 57 |
| Carnation | S | 92 | 90 | 93 | 93 | 92 | 90 | 87 | 88 | 85 | 83 | 80 | 79 | 78 | 71 | 70 | 70 | 68 | 51 | 38 | 27 | 19 | 11 | 8 |
| | N | 95 | 96 | 93 | 93 | 94 | 94 | 92 | 91 | 92 | 90 | 89 | 88 | 84 | 82 | 81 | 80 | 80 | 76 | 74 | 73 | 60 | 49 | 38 |

[*]100 seeds/plant/treatment
S = surface-sterilized
N = non-sterilized
[†]Chemical agent for these experiments comprised methylchloroisothiazolinone, methylisothiazolinone, magnesium chloride, magnesium nitrate, potassium sorbate and sodium benzoate. Culture media comprising this chemical agent were autoclaved.

TABLE 2

Formation Of Shoots And Roots In Plant Tissue Culture Media Containig Increasing Concentrations Of Chemical Agent

| Plant Type[*] | Percent Concentration Of Chemical Agent (v/v)[†] | | | | | | | | | | | |
|---|---|---|---|---|---|---|---|---|---|---|---|---|
| | 0 | 0.01 | 0.02 | 0.03 | 0.04 | 0.05 | 0.06 | 0.07 | 0.08 | 0.09 | 0.1 | 0.125 |
| Cucumber | S/R | S/R | S/R | S/R | S/R | S/R | S/R | S/R | S/R | S/R | S/R | S/R |
| Morning Glory | S/R | S/R | S/R | S/R | S/R | S/R | S/R | S/R | S/R | S/R | S/R | S/R |
| Balsam | S/R | S/R | S/R | S/R | S/R | S/R | S/R | S/R | S/R | S/R | S/R | S/R |
| Pepper | S/R | S/R | S/R | S/R | S/R | S/R | S/R | S/— | S/— | S/— | S/— | S/— |
| Egg Plant | S/R | S/R | S/R | S/R | S/R | S/R | S/R | S/R | S/— | S/— | S/— | S/— |
| Marigold | S/R | S/R | S/R | S/R | S/R | S/R | S/— | S/— | S/— | S/— | S/— | S/— |
| Lotus | S/R | S/R | S/R | S/R | S/R | S/R | S/R | S/— | S/— | S/— | S/— | S/— |
| Cabbage | S/R | S/R | S/R | S/R | S/R | S/R | S/R | S/R | S/R | S/R | S/R | S/R |
| Daisy | S/R | S/R | S/R | S/R | S/R | S/R | S/R | S/R | S/— | S/— | S/— | S/— |
| Carnation | S/R | S/R | S/R | S/R | S/R | S/R | S/R | S/R | S/— | S/— | S/— | S/— |

| Plant Type[*] | Percent Concentration Of Chemical Agent (v/v)[†] | | | | | | | | | | |
|---|---|---|---|---|---|---|---|---|---|---|---|
| | 0.15 | 0.175 | 0.2 | 0.3 | 0.4 | 0.5 | 0.6 | 0.7 | 0.8 | 0.9 | 1.0 |
| Cucumber | S/R | S/R | S/R | S/— | S/— | S/— | S/— | S/— | S/— | S/— | S/— |
| Morning Glory | S/R | S/— | S/— | S/— | S/— | S/— | S/— | S/— | S/— | S/— | S/— |
| Balsam | S/R | S/— | S/— | S/— | S/— | S/— | S/— | S/— | S/— | S/— | S/— |
| Pepper | S/— | S/— | S/— | S/— | S/— | S/— | S/— | —/— | —/— | —/— | —/— |
| Egg Plant | S/— | S/— | S/— | S/— | S/— | S/— | S/— | —/— | —/— | —/— | —/— |
| Marigold | S/— | S/— | S/— | S/— | S/— | S/— | —/— | —/— | —/— | —/— | —/— |
| Lotus | S/— | S/— | S/— | S/— | S/— | S/— | —/— | —/— | —/— | —/— | —/— |
| Cabbage | S/R | S/R | S/R | S/— | S/— | S/— | S/— | S/— | S/— | S/— | S/— |
| Daisy | S/— | S/— | S/— | S/— | S/— | S/— | —/— | —/— | —/— | —/— | —/— |
| Carnation | S/— | S/— | S/— | S/— | S/— | S/— | S/— | —/— | —/— | —/— | —/— |

[*]100 seeds per treatment
[†]Chemical agent for these experiments comprised methylchloroisothiazolinone, methylisothiazolinone, magnesium chloride, magnesium nitrate, potassium sorbate and sodium benzoate. Culture media comprising this chemical agent were autoclaved.
S = normal formation of shoot
N = normal formation of root,
— = no growth or abnormal growth

What is claimed is:

1. A plant tissue culture medium comprising a chemical agent, which chemical agent comprises: methylchloroisothiazolinone in a concentration range of about 2.0 to about 2.6 g/l; methylisothiazolinone in a concentration range of about 0.6 to about 0.8 g/l; magnesium chloride in a concentration range of about 15.0 to about 30 g/l; and magnesium nitrate in a concentration range of about 15.0 to about 30 g/l; wherein the chemical agent is present in the plant tissue culture medium at a concentration that reduces or prevents microbial contamination of the plant tissue culture medium and allows for substantially normal germination of seeds or substantially normal growth or development of plants, plant organs, plant tissues or plant cells.

2. The plant tissue culture medium of claim 1, wherein the chemical agent further comprises potassium sorbate in a concentration range of about 15 to about 25 g/l.

3. The plant tissue culture medium of claim 1, wherein the chemical agent further comprises sodium benzoate in a concentration range of about 13 to about 27 g/l.

4. The plant tissue culture medium of claim 1, wherein the chemical agent further comprises potassium sorbate in a concentration range of about 15 to about 25 g/l and sodium benzoate in a concentration range of about 13 to about 27 g/l.

5. The plant tissue culture medium of claim 4, wherein the chemical agent is present in the plant tissue culture medium in a concentration range of about 0.01% (v/v) to about 0.20% (v/v).

6. The plant tissue culture medium of claim 4, wherein the chemical agent is present in the plant tissue culture medium in a concentration range of about 0.02% (v/v) to about 0.10% (v/v).

7. The plant tissue culture medium of claim 4, wherein the chemical agent is present in the plant tissue culture medium in a concentration range of about 0.03% (v/v) to about 0.05% (v/v).

8. The plant tissue culture medium of claim 1, wherein the chemical agent is present in the plant tissue culture medium in a concentration range of about 0.01% (v/v) to about 0.20% (v/v).

9. The plant tissue culture medium of claim 1, wherein the chemical agent is present in the plant tissue culture medium in a concentration range of about 0.02% (v/v) to about 0.10% (v/v).

10. The plant tissue culture medium of claim 1, wherein the chemical agent is present in the plant tissue culture medium in a concentration range of about 0.03% (v/v) to about 0.05% (v/v).

11. A kit for germinating a plant seed or culturing a plant, plant organ, plant tissue or plant cell in vitro, which kit comprises:

(a) a culture container;

(b) a plant seed, plant, plant tissue, plant organ or plant cell; and (c) the plant tissue culture medium of claim 1, 2, 3, 4, 5, 6, 7, 8, 9, or 10.

12. The kit of claim 11, wherein the seed, plant, plant organ, plant tissue or plant cell is from a species of plant selected from the group consisting of cucumber, Morning Glory, balsam, pepper, eggplant, marigold, lotus, cabbage, daisy and carnation.

13. A method for reducing or preventing microbial contamination in a plant tissue culture medium, comprising adding to the medium a chemical agent, which agent comprises methylchloroisothiazolinone in a concentration range of about 2.0 to about 2.6 g/l; methylisothiazolinone in a concentration range of about 0.6 to about 0.8 g/l magnesium chloride in a concentration range of about 15.0 to about 30.0 g/l; and magnesium nitrate in a concentration range of about 15.0 to about 30.0 g/l; wherein the agent, after addition to the plant tissue culture medium, is present at a concentration that reduces or prevents microbial contamination of the plant tissue culture medium and allows for substantially normal germination of seeds or substantially normal growth or development of plants, plant organs, plant tissues or plant cells.

14. The method of claim 13, wherein the chemical agent further comprises potassium sorbate in a concentration range of about 15 to about 25 g/l.

15. The method of claim 13, wherein the chemical agent further comprises sodium benzoate in a concentration range of about 13 to about 27 g/l.

16. The method of claim 13, wherein the chemical agent further comprises potassium sorbate in a concentration range of about 15 to about 25 g/l and sodium benzoate in a concentration range of about 13 to about 27 g/l.

17. The method of claim 13, 14, 15 or 16, wherein the chemical agent is present in the plant tissue culture medium in a concentration range of about 0.01% (v/v) to about 0.20% (v/v).

18. The method of claim 13, 14, 15 or 16, wherein the chemical agent is present in the plant tissue culture medium in a concentration range of about 0.02% (v/v) to about 0.10% (v/v).

19. The method of claim 13, 14, 15 or 16, wherein the chemical agent is present in the plant tissue culture medium in a concentration range of about 0.03% (v/v) to about 0.05% (v/v).

* * * * *